United States Patent [19]

Zorayan et al.

[11] Patent Number: 4,612,188
[45] Date of Patent: Sep. 16, 1986

[54] COSMETIC COMPOSITIONS WHICH CONTAIN BIS-(QUATERNARY AMMONIUM) DERIVATIVES WITH TWO LIPOPHILIC CHAINS AND CERTAIN SAID DERIVATIVES

[75] Inventors: Vahan Zorayan, Enghien les Bains; Claire Fiquet, Paris, both of France

[73] Assignee: L'Oreal, Paris, France

[21] Appl. No.: 187,954

[22] Filed: Sep. 16, 1980

[30] Foreign Application Priority Data

Sep. 17, 1979 [LU] Luxembourg ............ 81694

[51] Int. Cl.$^4$ .............. A61K 7/06; A61K 7/09; A61K 7/11; A61K 7/13
[52] U.S. Cl. .................. 424/47; 8/406; 8/407; 132/7; 424/DIG. 2; 424/DIG. 4; 424/59; 424/62; 424/69; 424/70; 424/71; 424/72; 514/852; 514/864; 544/386; 564/160
[58] Field of Search .......... 564/160; 544/386; 424/70, DIG. 4, 71, 72, 47, 62; 132/7; 8/406, 407

[56] References Cited

U.S. PATENT DOCUMENTS

| | | | |
|---|---|---|---|
| 2,130,948 | 9/1938 | Carothers | 544/386 |
| 2,262,357 | 11/1941 | DeGroote et al. | 544/386 X |
| 2,310,873 | 2/1948 | Sauer | 564/160 |
| 2,328,551 | 9/1943 | Gunderson | 564/160 X |
| 2,984,539 | 5/1961 | Matter et al. | 564/160 X |
| 2,984,587 | 5/1961 | Matter et al. | 564/160 X |
| 3,196,156 | 7/1965 | Inaba et al. | 544/386 X |
| 3,198,660 | 8/1965 | Vail et al. | 564/160 X |
| 3,314,921 | 4/1967 | Berchtold | 564/160 |
| 3,869,483 | 3/1975 | Mod et al. | 544/386 |
| 4,013,787 | 3/1977 | Vanlerberghe | 424/DIG. 4 |
| 4,150,115 | 4/1979 | Jacquet et al. | 424/DIG. 4 |
| 4,247,476 | 1/1981 | Haase et al. | 564/160 X |

FOREIGN PATENT DOCUMENTS

| | | | |
|---|---|---|---|
| 531926 | 10/1956 | Canada | 564/160 |
| 874032 | 8/1961 | United Kingdom | 564/160 |
| 1109837 | 4/1968 | United Kingdom | 544/386 |

*Primary Examiner*—Dale R. Ore
*Attorney, Agent, or Firm*—Cushman, Darby & Cushman

[57] ABSTRACT

The invention relates to cosmetic compositions which are intended to be used for the treatment of keratin substances. These compositions contain at least one bis(quaternary ammonium) derivative with two lipophilic chains, corresponding to the formula

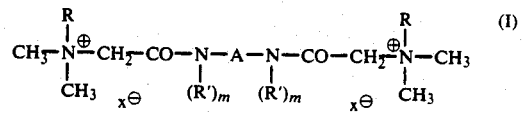

in which R denotes a saturated or unsaturated, linear or branched aliphatic group having from 8 to 22 carbon atoms, or a mixture of such groups, or mixtures of lipophilic chains derived from natural products having from 8 to 30 carbon atoms, A denotes a group $-(CH_2)_n-$, in which n denotes and integer from 1 to 18, R' denotes hydrogen and m=1, it also being possible for A to form a heterocyclic group together with the nitrogen atoms to which it is bonded, in which case m=O, and $X^-$ denotes and anion derived from a mineral or organic acid.

27 Claims, No Drawings

COSMETIC COMPOSITIONS WHICH CONTAIN BIS-(QUATERNARY AMMONIUM) DERIVATIVES WITH TWO LIPOPHILIC CHAINS AND CERTAIN SAID DERIVATIVES

DESCRIPTION

The present invention relates to compositions which contain quaternary ammonium derivatives and which are intended for the treatment of keratin substances, such as the hair and skin.

Compositions, in particular cosmetic compositions, which are intended to be used for the treatment of the hair and which are based on quaternary ammonium derivatives are already known. These compositions, which are used in particular as post-shampoo rinsing products, are generally presented in the form of a milky liquid, a balm or a cream; they have the disadvantage of weighing down the treated hair, this resulting from both the nature of the quaternary ammonium derivatives used and from the adjuvants required to impart the desired appearance and viscosity, and also the desired softness effects, to these derivatives.

Furthermore, because of their weighing-down effects, these compositions are preferably used only in the treatment of dry or damaged hair.

We have now discovered, according to the present invention, that the use of a particular class of water-soluble bis-(quaternary ammonium) derivatives with two lipophilic chains makes it possible to prepare compositions which are intended to be used for the treatment of keratin substances and which can be presented in limpid, fluid and optionally thickened formulations.

Bis-(quaternary ammonium) derivatives have principally been proposed for use in the dyeing of polyacrylonitrile fibres or in the treatment of synthetic or cellulosic textile materials.

We have discovered that the use of compositions containing bis-(quaternary ammonium) derivatives with two lipophilic chains, for the treatment of natural keratin substances, especially human hair, imparts more lightness to the hair than the use of the quaternary ammonium derivatives previously proposed for this purpose; these compositions can thus be applied to any type of hair (dry, normal or naturally greasy hair).

The compounds used in the present invention can be used in very small amounts for improving the combing-out, the softness and the glossiness of the hair, and they also possess a good tolerance.

The invention thus relates to compositions which are intended to be used for the treatment of natural keratin substances and which contain at least one bis-(quaternary ammonium) derivative with two lipophilic chains as well as to processes for the treatment of natural keratin substances with the abovementioned compositions.

The cosmetic compositions which are intended to be used for the treatment of natural keratin substances, according to the invention, are essentially characterised in that they contain, in a medium suitable for the treatment of these substances, at least one bis-(quaternary ammonium) derivative with two lipophilic chains, corresponding to the formula

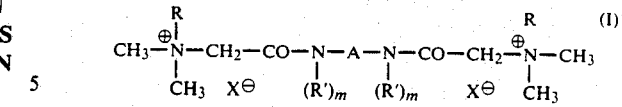

in which R denotes a saturated or unsaturated, for example ethylenically unsaturated, linear or branched aliphatic group having 8 to 22 carbon atoms, or a mixture of such groups, or one or more fatty chains, typically alkyl or alkenyl chains, derived from natural products having from 8 to 30 carbon atoms, A denotes either the group $-(CH_2)_n-$, in which n denotes an integer from 1 to 18, R' denotes hydrogen and m=1, or a heterocyclic group together with the nitrogen atoms to which it is bonded, in which case m=O, and $X^-$ denotes an anion derived from a mineral or organic acid, preferably a halide.

The compounds which are more particularly preferred according to the invention are those in which R denotes a linear or branched alkyl or alkenyl group having 12 to 18 carbon atoms, or a mixture of such groups, and those in which R represents a mixture of aliphatic groups derived from fatty chains of natural products, such as tallow, copra and lanoline.

If A forms a heterocyclic group together with the adjacent nitrogen atoms, it preferably denotes a piperazinyl group.

The invention also provides, as new compounds, the compounds of formula (I) with the proviso that n is greater than 3 if R denotes an alkyl group having 10 to 18 carbon atoms.

These compounds can be prepared in accordance with reaction processes which are in themselves known and which consist, in particular, in condensing two mols of a tertiary amine of the formula

with one mol of a derivative corresponding to the formula

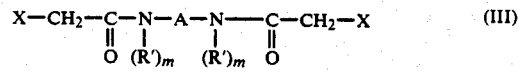

in which X denotes an electronegative substituent, preferably a halogen atom.

The compounds which are more particularly preferred according to the invention result from the condensation of bis-chloroacetyl-1, 3-diaminopropane, bis-chloroacetylpiperazine, bis-chloroacetylethylenediamine or bis-chloroacetylhexamethylenediamine with N,N-dimethyl-tallow alkyl-amine or with N,N-dimethylalkyl ($C_{12}$-$C_{14}$)-amine.

As indicated above, the compounds corresponding to the formula (I) possess valuable properties when used in the treatment of natural keratin substances and in particular hair.

The invention thus relates to the use of the compounds of the formula (I) for the treatment of keratin substances, such as hair, skin, fingernails and body hair.

The compositions which are intended for use in the treatment of the abovementioned keratin substances are preferably aqueous compositions which can be used as such; however, they can also contain adjuvants which are normally used in compositions for the treatment of keratin substances.

The most valuable results have been observed in the application of these compounds in the treatment of the hair. In this case, these cosmetic compositions are typically presented in the form of an aqueous, alcoholic or aqueous-alcoholic solution or in the form of a cream, a gel, an emulsion or a powder, or they can be packaged in an aerosol in the presence of a propellant.

The adjuvants present in these compositions are cosmetically acceptable adjuvants, such as non-ionic, anionic, cationic or amphoteric surface-active agents which are well known in the art, animal, mineral, vegetable or synthetic oils or waxes, fatty alcohols, anionic, cationic, non-ionic or amphoteric resins which are normally used in cosmetics, emulsifiers, sun filters, organic solvents, thickeners, opacifying agents, preservatives, sequestering agents, antioxidants, perfumes, agents for imparting pearlescence, dyestuffs, pH modifiers, reducing agents, electrolytes, oxidizing agents, natural substances, protein derivatives, anti-seborrhea agents, anti-dandruff agents, restructuring agents, and active substances which can have an action in the treatment, care or protection of the skin or hair.

These compositions can be used, in particular, as shampoos, as coloring products, as rinsing lotions to be applied before or after shampooing, before or after coloring or bleaching, or before or after perming, as styling or restructuring lotions, as treating lotions, such as anti-seborrhea or anti-dandruff lotions, as brushing lotions, as hair lacquers, as wavesetting lotions and as perming compositions.

When the compounds are applied in the treatment of the hair, either in pre-treating or post-treating lotions, or during the actual treatment, such as shampooing, dyeing, bleaching, wavesetting or perming, they substantially improve the properties of the hair by facilitating the combing-out of the hair when wet or dry, and by imparting glossiness, softness, suppleness, manageability and antistatic properties to the hair when dry. The hair treated in this way is light, springy and bulky, these being desirable properties for normal or naturally greasy hair.

The bis-(quaternary ammonium) derivatives with two lipophilic chains, of the formula I, should, of course, be used in the compositions according to the invention in sufficient amounts to obtain the desired result, generally in an amount from 0.01 to 10% by weight, preferably 0.1 to 4% by weight.

In particular, these compounds are very valuable when used as pre-treating agents before an anionic and/or non-ionic shampoo or before an oxidation dyestuff, the latter itself being followed by an anionic and/or non-ionic shampoo.

Significantly advantageous results can also be observed when these compounds are used as pre-treating agents in other hair-treatment processes, such as perming.

The bis-(quaternary ammonium) derivatives with two lipophilic chains, of the formula (I), also give very advantageous results when used as post-treating agents and in particular as post-shampoo rinsing lotions and as wavesetting or shaping lotions, restructuring lotions, brushing lotions, styling gels and treating lotions.

The cosmetic compositions for the hair, according to the invention, include in particular:

(a) Compositions for the treatment or the pre-treatment or post-treatment of the hair. The application of these compositions to the hair is optionally followed by rinsing, after an interval of, say, 1 to 30 minutes.

The compounds of the formula (I) are preferably present in a proportion of 0.01 to 10% by weight, preferably 0.1 to 4% by weight, expressed in terms of active ingredient, relative to the total weight of the composition. The pH is generally from 2 to 10. The treating compositions or pre-treating or post-treating compositions can contain various adjuvants, in particular polyethylene glycols and their derivatives, anionic, cationic, amphoteric or non-ionic resins which are normally used in cosmetic compositions for the hair, pH modifiers, protein derivatives, such as quaternized or non-quaternised protein hydrolysates, natural substances, such as plant extracts, fatty alcohols, such as optionally polyoxyethyleneated or polyglycerolated cetyl, stearyl, cetyl/stearyl or oleyl alcohol, animal, vegetable, mineral or synthetic oils or waxes, such as optionally oxyethyleneated petrolatum, maize oil, wheatgerm oil, olive oil, soya bean oil, castor oil or avocado oil, substances active on the hair, such as anti-seborrhea or anti-dandruff products, hair-restructuring agents, such as methylolated derivatives, and other cosmetic adjuvants which are normally used in cosmetic compositions for the hair.

(b) Shampoos which are essentially characterized in that they contain at least one anionic, non-ionic or amphoteric surface-active agent or a mixture thereof, and a compound of the formula (I), in an aqueous medium. These compositions can also contain various adjuvants which are normally used in this type of composition, such as cationic surface-active agents, dyestuffs in the case of coloring shampoos, preservatives, thickeners, foam stabilizers, synergistic agents, softening agents, sequestering agents, one or more cosmetic resins, perfumes, protein derivatives, natural substances and oils. In these shampoos, the concentration of detergent is generally 2 to 50% by weight.

Amongst the non-ionic detergents, there may be mentioned, in particular, the products resulting from the condensation of a monoalcohol, an alpha-diol, an alkylphenol, an amide or a diglycolamide with glycidol, such as the non-ionic surface-active agents described in French Pat. Nos. 2,091,516, 2,328,763 and 1,477,048, and also polyoxyethyleneated or polyglycerolated alcohols, alkylphenols or fatty acids with linear fatty chains having 8 to 18 carbon atoms and most frequently containing 2 to 30 mols of ethylene oxide, copolymers of ethylene oxide and propylene oxide, products resulting from the condensation of ethylene oxide and propylene oxide with fatty alcohols, polyoxyethyleneated fatty amides, polyoxyethyleneated fatty amines, ethanolamides, fatty acid esters of glycol, fatty acid esters of sorbitol and fatty acid esters of sucrose.

The anionic surface-active agents, which can optionally be used with the non-ionic surface-active agents, are chosen, in particular, from amongst the alkali metal salts, the ammonium salts, the amine salts or the aminoalcohol salts of the following compounds: alkyl-sulphates, alkyl-ether-sulphates, alkylamide-sulphates and alkylamido-ether-sulphates, alkylaryl-polyethersulphates and monoglyceride-sulphates; alkyl-sulphonates, alkylamidesulphonates, alkylarylsulphonates and α-olefinesulphonates; alkylsulphosuccinates, alkyl-ethersulphosuccinates and alkylamide-sulphosuccinates; alkylsulphosuccinamates; alkyl-sulphoacetates and alkylpolyglycerol-carboxylates; alkyl-phosphates and alkyl-etherphosphates; alkylsarcosinates, alkylpolypeptidates, alkylamidopolypeptidates, alkylisethionates and alkyl-taurates, the alkyl radical in all these compounds being a linear chain having 12 to 18 carbon atoms, and fatty acids, such as oleic acid, ricinoleic acid, palmitic acid, stearic acid, acids derived from copra oil or from hydrogenated copra oil, and carboxylic acids of polyglycol ethers, corresponding to the formula:

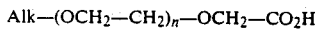

Alk—(OCH$_2$—CH$_2$)$_n$—OCH$_2$—CO$_2$H in which the substituent Alk corresponds to a linear chain having from 12 to 18 carbon atoms and in which n is an integer from 5 to 15. it is of course also possible to use other anionic detergents well known in the art.

Amongst the amphoteric surface-active agents which can be used, there may be mentioned, more particularly, alkylamino-monopropionates and -dipropionates of betaines such as N-alkylbetaines, N-alkylsulphobetaines and N-alkylamidobetaines, cycloimidinium compounds, such as alkylimidazolines, and asparagine derivatives. The alkyl group in these surface-active agents preferably possesses 1 to 22 carbon atoms.

(c) Hair-dyeing compositions, such as dyeing compositions which function by an oxidation method and contain oxidation dyestuff precursors, such as those of the para- or ortho-type, and optionally couplers, in a medium which is basic and preferably has a pH of 8 to 11, and which can also contain direct dyestuffs which are well known in the art, or dyeing compositions which are intended for direct or semi-permanent coloration and contain direct dyestuffs, such as nitrobenzene derivatives, azo dyestuffs, anthraquinone dyestuffs, indamines, indoanilines or indophenols.

(d) Bleaching compositions which consist of carriers in the form of powders, solutions, emulsions or gellable liquids, or in the form of creams, containing at least one bleaching agent, such as hydrogen peroxide or other peroxides or solutions of per-salts(e.g. persulphates, perborates or percarbonates), and at least one compound of the formula (I).

Preferably, the bleaching compositions are in the form of creams or gellable liquids, which are similar to those described above in the context of the dyeing compositions. These are intended to be diluted at the time of use with a solution of hydrogen peroxide and/or of per-salts and/or of other peroxides.

The carriers generally contain an alkalizing agent, such as ammonia.

These bleaching compositions can be applied using conventional techniques.

(e) Perming compositions.

It is known that the conventional technique for perming the hair consists, in a first stage, in opening the S—S bonds in the keratin of the hair, using a composition containing a reducing agent, and then, in a second stage, preferably after having rinsed the head of hair, in re-forming the said S—S bonds by applying an oxidizing composition to the hair which has been subjected to reduction, so as to impart the desired shape to the hair.

The formulation of the said reducing and oxidizing (neutralizing) compositions is known and is described in the works on cosmetology, in particular by E. SIDI and C. ZVIAK, Problèmes Capillaires (Hair Problems), Paris 1966 (GAUTHIER-VILLARD).

According to this aspect of the invention, at least one of these two compositions contains a compound of the formula (I). In addition to the reducing agent, the reducing compositions generally contain the adjuvants which make it possible to present them in the form of lotions or in the form of a powder to be diluted in a liquid carrier. The reducing agent is most frequently a mercaptan, such as thioglycerol or thioglycolic acid or a derivative thereof.

The concentration of the reducing agent is the concentration which is required to reduce a sufficient number of S—S bonds. These concentrations are well known and are described in standard works on cosmetology. For example, in the case of thioglycolic acid, the concentration is generally 1 to 11% by weight.

The pH of these compositions for the first stage of perming generally varies from 7 to 10. The reducing compositions generally contain from 0.1 to 10% by weight, in particular 0.25 to 5%, of a compound of the formula (I).

These reducing lotions for the first stage of perming are most frequently aqueous solutions which can also contain pH modifiers, auxiliary reducing agents, such as sulphites, solvents, such as ethanol or isopropanol surface-active agents, perfumes and/or dyestuffs.

In addition to the oxidizing agent, the oxidizing or neutralizing compositions applied in a second stage can contain the compound of the formula (I) and optionally conventional adjuvants.

The compounds of the formula (I) can of course be used in all cosmetic formulations as an additive for imparting characteristics of easy combing-out, softness, glossiness and lightness to the hair, in addition to the properties which the compositions themselves are intended to impart.

The compositions according to the invention can also be applied to the skin and can adopt the various forms mentioned above; the quaternary ammonium derivatives give the skin a softness to the touch.

In addition to the compounds of the formula (I), such compositions can contain the various cosmetic adjuvants which are normally used for the skin, in particular perfumes, dyestuffs, preservatives, sequestering agents, emulsifying agents, thickeners and sun filers.

The compositions constitute, in particular, treating creams or lotions for the hands or face, anti-sunburn creams, tinted creams, milks for removing make-up, shaving creams, foaming oils or liquids for the bath or shower, and deodorizing compositions, which can be prepared in accordance with conventional processes.

It should be noted that the compounds according to the invention also possess other advantageous properties, such as bacteriostatic properties and surface-active properties.

The following Examples further illustrate the present invention.

PREPARATION EXAMPLE 1

22.7 g (0.1 mol) of bis-chloroacetyl-1,3-diaminopropane (molecular weight 227) and 59.12 g (0.2 mol) of N,N-dimethyl-tallow alkyl-amine (molecular weight 295.6) are introduced into 246 g of distilled water at 85° C.-90° C.

The mixture of amine and chlorine derivative is heated to 95° C. The reaction is highly exothermic and sudden thickening of the mixture takes place. Hot distilled water is added and the whole is kept at 90°-95° C. for one hour. The mixture becomes homogeneous and viscous.

The acid number is 0.52, the amine number is 2.36 and the extent of reaction is 94%.

On keeping the mixture at 95° C. for a further one hour, an acid number of 0.9, an amine number of 0.75 and an extent of reaction of 97.7% are observed.

The bis-quaternary compound prepared in this way corresponds to the formula

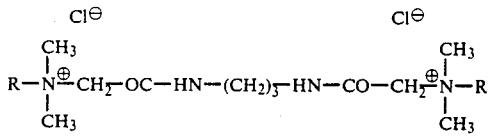

in which R denotes a tallow alkyl chain.

A tallow alkyl chain denotes a mixture of alkyl or alkenyl radicals having 10 to 20 carbon atoms, this mixture essentially comprising saturated groups having 16 carbon atoms and mono-, di- or tri-unsaturated groups having 18 carbon atoms.

PREPARATION EXAMPLE 2

57.2 g (0.2 mol) of N,N-dimethyl-tallow alkylamine, having a molecular weight of 295.6, and 21.1 g (0.1 mol) of bis-chloroacetylpiperazine are introduced into 148 g of distilled water at 85°–90° C.

A further 2.65 g and 0.65 g of the bis-chloroacetylpiperazine derivative are added during the reaction. The mixture of amine and bis-chloroacetylpiperazine is heated to 90°–95° C. under nitrogen.

The reaction is exothermic and the temperature rises to 100°–101° C., thickening of the mixture taking place.

Water at 85°–90° C. is added and the whole is kept at 90°–95° C. for 1 hour 30 minutes to 2 hours.

The acid number is 6.4 and the amine number is 1.1.

On adding 3.3 g of bis-chloroacetylpiperazine and keeping the mixture at 95° C. for 2 hours to 2 hours 30 minutes, a compound is obtained which has an acid number of 1.5, an amine number of 1.4 and an extent of reaction of 97.2%, and which corresponds to the formula

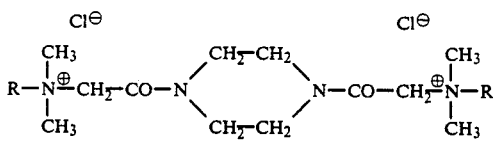

in which R denotes a tallow chain.

The solution thus obtained is a viscous solution.

PREPARATION EXAMPLE 3

53.25 g (0.25 mol) of bis-chloroacetylethylenediamine and 143.15 g (0.5 mol) of N,N-dimethyl-tallow alkylamine (molecular weight 286.3) are introduced into 560 g of distilled water at 85° C.

The mixture of chlorine derivative and amine is heated to 90° C. in the course of one hour, under nitrogen, and is kept at 90°–95° C. for 1 hour 30 minutes.

The reaction is exothermic and the mixture thickens.

Hot distilled water is then added; the product dissolves to give a viscous and limpid mixture. The extent of reaction is 75–77% at this point. On keeping the mixture at 95° C. for 3 hours, an acid number of 0.7, an amine number of 1.2 and an extent of reaction of 97.2% are observed.

A 26.3% strength solution is in the form of a gel when cold.

The compound prepared in this way corresponds to the formula

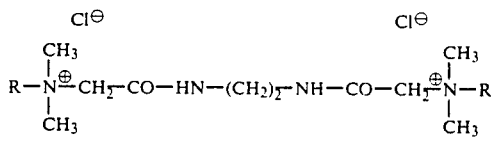

in which R is a tallow chain.

PREPARATION EXAMPLE 4

20 g (0.0743 mol) of bis-chloroacetylhexamethylenediamine and 43.95 g (0.1468 mol) of N,N-dimethyl-tallow alkyl-amine, having a molecular weight of 295.6, are introduced into 149 g of distilled water at 85°–90° C.

The mixture of amine and chlorine derivative is heated to 95° C.

After 10 minutes, substantial exothermicity is observed and the temperature rises to 105° C. The mixture is diluted rapidly with hot water and the diluted mixture is kept at 95° C. for 2 hours.

An amine number of 2.12, an acid number of 0.85 and an extent of reaction of 95% are observed.

The product thus obtained corresponds to the formula

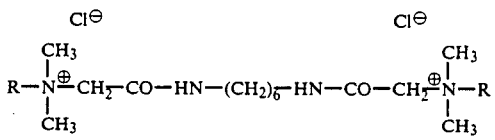

in which R denotes a tallow chain.

PREPARATION EXAMPLE 5

47.2 g (0.2 mol) of a mixture of dimethylalkylamine (alkyl is a mixture of $C_{12}$–$C_{14}$ alkyl groups) (molecular weight 236) and 26.9 g (0.1 mol) of bis-chloroacetylhexamethylenediamine (molecular weight 269) are introduced into 173 g of distilled water at 85° C.

The mixture of amine and halogen derivative is heated to 90°–95° C.

The reaction is exothermic, the temperature rises to 106° C. and the mixture thickens considerably.

Distilled water is added rapidly and the mixture is kept at 90° C. for 2 hours.

The acid number is 0.77, the amine number is 1.5 and the extent of reaction is 97%.

The compound prepared in this way corresponds to the formula

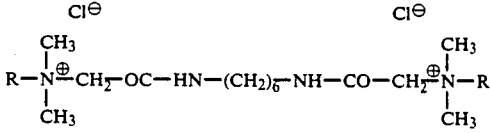

in which R denotes a mixture of alkyl chains having 12 to 14 carbon atoms.

By proceeding in an identical manner, but using, as the starting product, the dimethylalkylamine in which alkyl denotes a total copra residue, a compound is obtained which possesses the same characteristics as the compound of Example 5 above.

The following Examples illustrate cosmetic compositions according to the invention and the hair-treatment processes using these compositions.

EXAMPLE 1

POST-SHAMPOO HAIR MILK

The following composition is prepared:
Cetyl alcohol: 12 g
Vaseline oil: 25 g
Partially oxyethyleneated cetyl/stearyl alcohol: 30 g
26.3% strength solution of the compound of the formula

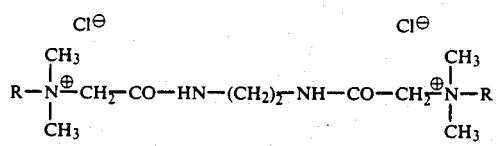

in which R denotes a tallow chain: 35 g
Water q.s.p.: 1,000 g.

This composition, which is used as a post-shampoo composition, is opaque, white in color and fluid, and has a viscosity of about 25 cps and a pH of 4.4. After the hair has been washed with a shampoo, rinsed and towel-dried, the hair milk described above is applied to the clean hair.

This composition is appropriately spread over the whole head of hair and, after an interval of about 10 minutes, the hair is rinsed very carefully. When wet, the hair is easy to comb out and is soft to the touch. When dry, the hair is also easy to comb out and is soft, glossy, manageable, uncharged with static electricity and light.

EXAMPLE 2

POST-SHAMPOO BALM

The following composition is prepared:
Cetyl alcohol: 7 g
Stearyl alcohol: 7 g
Oleyl alcohol: 15 g
Polawax GP 200: 25 g
34.1% strength solution of the compound of the formula

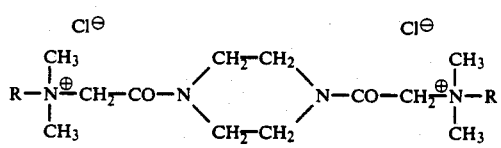

in which R = tallow chain: 20 g
Citric acid: 2 g
Water q.s.p.: 1,000 g

This composition, which is used as a post-shampoo composition, is opaque, white in color and unctuous. It has a viscosity of about 400 cps. The pH of this product is 2.7. On applying this composition in accordance with the same procedure as that described in Example 1, it is also observed that, when wet, the hair is easy to comb out and is soft to the touch, and that, when dry, the hair is glossy, soft, easy to comb out and manageable.

EXAMPLE 3

POST-SHAMPOO HAIR MILK

The following composition is prepared:
Alfol C16/C18: 32 g
Cellosize QP 4400 H: 3.5 g
29% strength solution of the compound corresponding to the formula

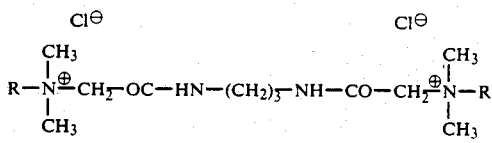

in which R denotes a tallow chain: 24 g
Crotein Q (Croda): 9 g
Water q.s.p.: 1,000 g This composition is used as a post-shampoo hair milk. It is white in color and is fairly fluid, the viscosity being about 55 cps, and the pH is 6.1. In the same way as previously, it is found that the application of these compounds to the hair imparts a soft feel to the hair when wet, and, when dry, the hair is easy to comnb out, glossy, soft, manageable and uncharged with static electricity.

EXAMPLE 4

HAIR OIL

The following composition is prepared:
Oxyethyleneated castor oil: 200 g
Avocado oil: 40 g
Solution (26.3% strength) of the compound of the formula

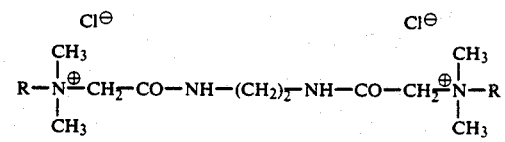

in which R = tallow chain: 40 g
Water q.s.p.: 1,000 g
The pH is 4.9.

This hair oil has the appearance and consistency of an oil, is limpid and of low viscosity and has a greasy feel.

This oil is applied after shampooing, and, after an interval of a few minutes, followed by rinsing, the treated hair is easy to comb out, glossy, manageable and bulky. This composition can also be applied before shampooing, and left on the hair for an interval of 1 to 30 minutes.

EXAMPLE 5

HAIR OIL

The following composition is prepared:
Oxyethyleneated castor oil: 300 g
Avocado oil: 20 g
Solution, containing 30% of solids, of the compound corresponding to the formula

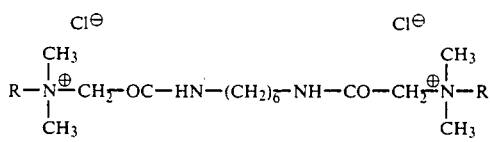

in which R=mixture of alkyl chains ($C_{12}$–$C_{14}$): 25 g
Dyestuff, perfume and preservative q.s.
Water q.s.p.: 1,000 g In a similar application to that indicated for Example 4, identical results are observed.

Similar results are observed by using, in place of the bis-quaternary compound, a compound which has the same formula but in which R denotes a total copra residue.

EXAMPLE 6

HAIR OIL

The following composition is prepared:
Oxyethyleneated castor oil: 220 g
Castor oil: 8 g
26.3% strength solution of the compound corresponding to the formula

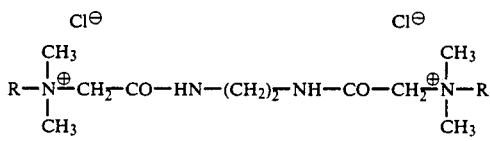

in which R=tallow chain: 20 g
Water q.s.p.: 1,000 g

This oil is applied to wet hair before shampooing, and left on the hair for an interval of about 20 minutes.

The hair is rinsed and then washed with a conventional shampoo and it is found that, when dry, the hair is easy to comb out, glossy and soft to the touch, has a good hold and is bulky.

EXAMPLE 7

FLUID BALM

The following composition is prepared:
29% strength solution of the compound prepared in Preparation Example 1, of the formula

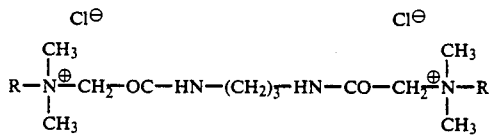

in which R=tallow chain: 15 g
Protein hydrolysate: 5 g
Gafquat 755: 8 g
Water q.s.p.: 1,000 g This balm has a very fluid, limpid appearance and a pH of 5.7.

This composition is applied to clean wet hair which has been washed with a shampoo beforehand.

After application to the hair and after an interval of 10 minutes, followed by rinsing, it is found that, when dry, the hair is easy to comb out without being weighed down or flattened.

Similar results are observed when using the compositions of Examples 8 and 9 which follow.

EXAMPLE 8

LIMPID POST-SHAMPOO COMPOSITION

The following composition is prepared:
Cellosize QP 4400 H: 10 g
Dyestuff, perfume and preservative q.s.
Solution, containing 29% of solids, of the compound of the formula

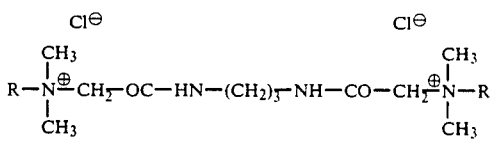

in which R=tallow chain: 20 g
Protein hydrolysate: 10 g
Water q.s.p.: 1,000 g

This composition is in the form of a limpid fluid gel having a viscosity of about 200 cps.

EXAMPLE 9

LIMPID POST-SHAMPOO COMPOSITION

The following composition is prepared:
Cellosize QP 4400 H: 10 g
Gafquat 755: 10 g
Solution, containing 30% of solids, of the compound corresponding to the formula

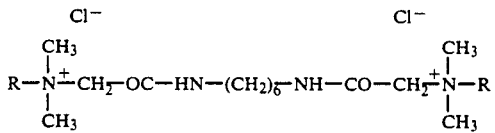

in which R=mixture of alkyl chains ($C_{12}$–$C_{14}$): 20 g
Water q.s.p.: 1,000 g

EXAMPLE 10

PRE-SHAMPOO LOTION

The following composition is prepared:
Merquat 100: 2.5 g
Solution, containing 34.1% of solids, of the compound prepared in Preparation Example 2, of the formula

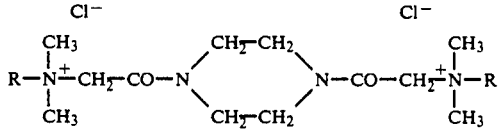

in which R=tallow chain: 30 g
Water q.s.p.: 1,000 g

This composition is in the form of a limpid treating lotion having a pH of 4.

This composition is applied to dirty hair before shampooing. After rinsing and after shampooing, it is found, in the same way as previously, that the hair is easy to comb out, supple and manageable, without being weighed down.

EXAMPLE 11

POST-SHAMPOO RINSING MILK FOR THE HAIR

The following composition is prepared:
Partially oxyethyleneated cetyl/stearyl alcohol: 30 g
Polawax GP 200: 30 g
Steary alcohol: 20 g
Solution, containing 30% of solids, of the compound prepared in Preparation Example 4, of the formula

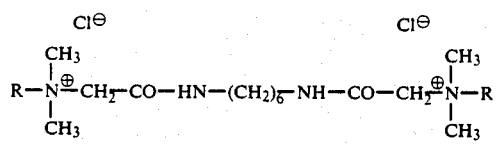

in which R=tallow chain: 40 g
Water q.s.p.: 1,000 g

This composition, which is used as a post-shampoo composition, has the appearnce of a white milk, a viscosity of about 380 cps after 24 hours and a pH of 5.

On applying this composition as described in Example 1, it is also observed that, when wet, the hair is easy to comb out and is soft to the touch, and that, when dry, the hair is glossy, manageable, uncharged with static electricity and soft to the touch and that it is easy to comb out.

EXAMPLE 12

POST-SHAMPOO FLUID BALM

The following composition is prepared:
Solution, containing 30% of solids, of the compound corresponding to the formula

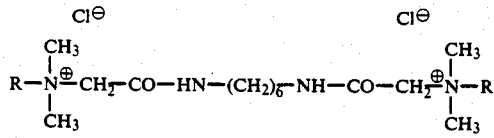

in which R=fatty chain: 23 g
Crotein Q: 7 g
Gafquat 755: 5 g
Water q.s.p.: 1,000 g This composition, which is used as a post-shampoo composition, is in the form of a limpid lotion having a pH of 6.35.

In the same way as previously, it is observed that the hair is easy to comb out, is soft to the touch and has a good hold.

EXAMPLE 13

ANIONIC SHAMPOO

The following composition is prepared:
Setacin 103 Spezial: 35 g
Compound of the formula

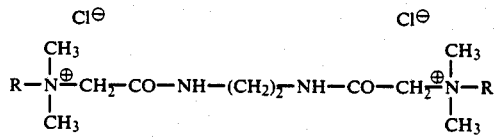

in which R=tallow chain: 0.5 g (active ingredient)
Methocel F 4M: 0.25 g
Formaldehyde: 0.06 g
Demineralised water q.s.p.: 100 g
The pH is adjusted to 6 with triethanolamine.

This composition has a liquid, limpid and fluid appearance.

About 10 cm$^3$ of this composition are applied to a head of hair which has been wetted beforehand. The hair is massaged lightly. It is rinsed with water, a second application is carried out, the hair is massaged vigorously in order to obtain a copious foam and, after an interval of a few minutes, the hair is rinsed.

When wet, the hair is easy to comb out; when dry, the hair is glossy, soft to the touch, light and springy and is easy to comb out.

EXAMPLE 14

NON-IONIC SHAMPOO

Surface-active agent of the formula:

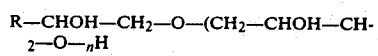

in which R is a mixture of $C_9$–$C_{12}$ alkyl radicals and n represents an average statistical value of about 3.5: 10 g
Compound of the formula

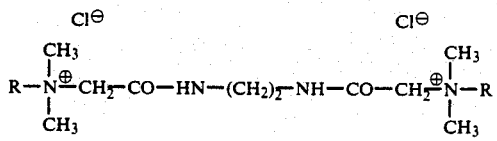

in which R=tallow chain: 1 g of active ingredient
Mono- and di-palmitostearate of PEG 6000, sold under this name by the Société Gattefossé: 2 g
Distearate of PEG 6000, sold under the name EMCOL L 32-45 by the Société Witco: 2 g
Formaldehyde: 0.06 g
Demineralized water q.s.p.: 100 g
The pH is adjusted to 5.

The shampoo has the appearance of a thickened limpid liquid.

After application as indicated in Example 13, similar results are observed.

EXAMPLE 15

CATIONIC SHAMPOO

Compound of the formula

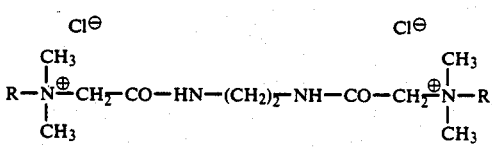

in which R is a tallow chain: 4 g of active ingredient
MIRANOL C2M: 8 g
Solution, containing 60% of active ingredient, of a non-ionic surface-active agent based on polyglycerolated lauryl alcohol (containing 4.2 mols of glycerol), of the formula

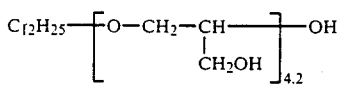

10 g

Demineralized water q.s.p.: 100 g

The pH is adjusted to 5 with HCl.

This composition has the appearance of a limpid gel.

In the same way as for hair washed with the shampoo of Examples 13 and 14, it is found that, when wet, the hair is easy to comb out, and that, when dry, the hair is glossy, soft and light.

EXAMPLE 16

STRUCTURING LOTION

Before use, 0.3 g of dimethylolethylenethiourea is mixed with 20 ml of a solution containing:

Compound of the formula:

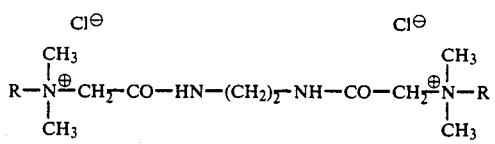

in which R is a tallow chain: 1 g (active ingredient)

Hydrochloric acid q.s.p.: pH 2.4

Water q.s.p.: 100 ml

The mixture is applied to hair which has been washed and towel-dried, before setting it in waves.

The hair is easy to comb out and soft to the touch. It is set in waves and dried.

EXAMPLE 17

OXIDATION DYE

The following composition is prepared:

Non-ionic surface-active agent of the formula

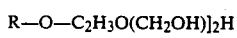

in which R denotes an oleyl group: 20 g

Non-ionic surface-active agent of the formula

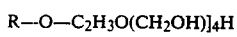

in which R denotes an oleyl group: 20 g

Oleyl diethanolamide: 12 g

Compound of the formula

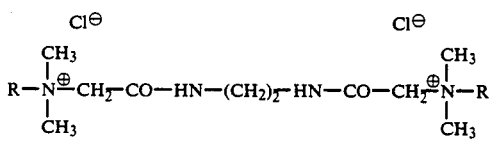

in which R is a tallow chain: 4 g (active ingredient)

96° strength ethyl alcohol: 12 g

Butylglycol: 1 g

Propylene glycol: 2 g

Pentasodium salt of diethylenetriaminopentaacetic acid (40% of active ingredient): 2.5 g 22° Bé strength ammonia solution: 9 ml 1-Amino-4-[(2-methoxyethyl)-amino]benzene dihydrochloride: 1.6 g p-Aminophenol: 0.3 g Resorcinol: 0.2 g m-Aminophenol: 0.25 g 5-[N-(2 Hydroxyethyl)-amino]-2-methylphenol: 0.02 g 1-(2-Hydroxyethoxy)-2,4-diaminobenzene dihydrochloride: 0.02 g Sodium bisulphite solution (d=1.32): 1 ml Water q.s.p.: 100 g 30 g of this carrier are mixed in a bowl with 30 g of hydrogen peroxide with 20 volumes strength. This gives a gel which is pleasant to apply and which adheres well to the hair. It is applied using a paintbrush and, after an interval of 30 to 40 minutes, the hair is rinsed. The hair is easy to comb out and has a silky feel and an ashen light chestnut shade is obtained.

EXAMPLE 18

COLORING COMPOSITION

The following composition is prepared:

Sinnowax AO: 2.00 g

Ukanil 25: 3.00 g

Ukanil 43: 2.00 g

1-Methoxy-3-nitro-4-[N-(β-hydroxyethyl)-amino]-benzene: 0.65 g

N$_4$-Methyl-2-nitro-1,4-diaminobenzene: 0.70 g

2-[N-(β-Aminoethyl)-amino]anthraquinone hydrochloride: 0.60 g

Compound of the formula

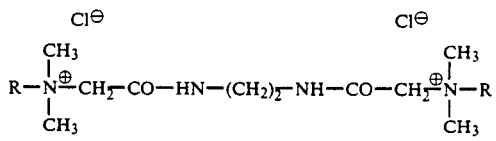

in which R is a tallow chain: 1 g (active ingredient)

Ethylcellosolve: 10 g

Triethanolamine q.s.p.: pH 7

Water q.s.p.: 100 g

This composition is applied to natural chestnut hair. After an interval of 10 minutes, the hair is rinsed; it is easy to comb out and has a soft feel. After wavesetting and drying, the hair has a particularly luminous mahogany sheen.

EXAMPLE 19

WAVESETTING LOTION

Polyvinylpyrrolidone: 1 g

Compound of the formula

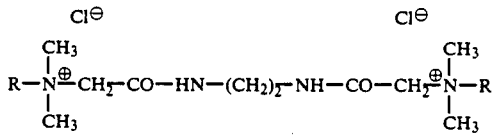

in which R is a tallow chain: 0.5 g (active ingredient)

Ethyl alcohol q.s.p.: 10% by volume

Perfume q.s.

Dyestuff q.s.

Water q.s.p.: 100 ml

This composition is applied to the hair. The hair is set in waves and dried; it is glossy and has volume and it is soft to the touch and easy to comb out.

EXAMPLE 20

REDUCING LIQUID FOR PERMING

Thioglycolic acid: 7 g
Ammonia solution q.s.: pH=7
Monoethanolamine q.s.: pH=9.2
Compound of the formula

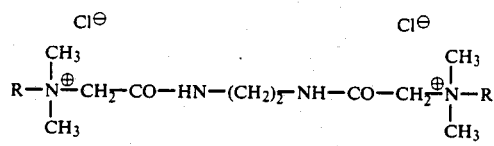

in which R is a tallow chain: 0.3 g (active ingredient)
Perfume q.s.
Dyestuff q.s.
Water q.s.p.: 100 ml

EXAMPLE 21

NEUTRALISER FOR PERMING

Compound of the formula

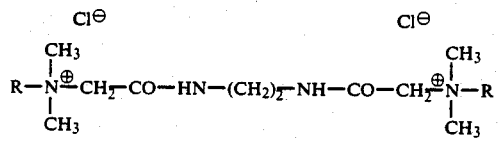

in which R is a tallow chain: 0.25 g
Phenacetin: 0.1 g
Citric acid: 0.3 g
Hydrogen peroxide q.s. 8 volumes strength
Dyestuff q.s.
Perfume q.s.
Water q.s.: 100 ml When carrying out a hair-perming treatment using either the composition of Example 20, as a reducing liquid applied in the first stage and followed by a conventional oxidizing treatment, or the composition of Example 21, as a neutralizing liquid preceded by reduction using a conventional reducing agent, or both the compositions of Examples 20 and 21 in succession, it is found that, in all cases, the treated hair is glossy, soft to the touch and light and the style has a good hold.

EXAMPLE 22

| TREATMENT LOTION FOR THE HANDS AND FACE | % by weight |
|---|---|
| autoemulsifiable glycerol stearate | 2 |
| cetyl alcohol | 1.5 |
| glycerol stearate | 2.5 |
| "Amerchol L 101" | 3 |
| perhydrosqualene | 15 |
| isopropyl myristate | 2 |
| "Natrosol 250 HHR" | 1 |
| methyl parahydroxybenzoate | 0.3 |
| 26.3% solution of the dry extract prepared according to preparation Example 3 | 7.5 |
| perfume | qs |
| water qsp | 100 |

This composition confers to the treated skin a softness to the touch.

EXAMPLE 23

| TINTED CREAM FOR THE FACE | % by weight |
|---|---|
| autoemulsifiable glycerol stearate | 3 |
| glycerol stearate | 2 |
| "Amerchol L 101" | 3 |
| isopropyl palmitate | 10 |
| propylene glycol | 3 |
| "Natrosol 250 HHR" | 1 |
| methyl parahydroxy benzoate | 0.3 |
| red iron oxide | 0.8 |
| yellow iron oxide | 0.6 |
| titanium dioxide | 1 |
| 26.3% solution of the dry extract of the product prepared in preparation Example 3 | 5.6 |
| perfume | 0.3 |
| water qsp | 100 |

EXAMPLE 24

| ANTISUN CREAM | % by weight |
|---|---|
| cetyl alcohol | 2 |
| autoemulsifiable glycerol stearate | 3 |
| glycerol stearate | 3 |
| lanoline | 2 |
| isopropyl myristate | 10 |
| "Natrosol 250 HHR" | 1 |
| methyl parahydroxybenzoate | 0.5 |
| 26.3% solution of the dry extract of the product obtained in preparation Example 3 | 12.3 |
| 2-ethoxyethyl p-methoxy cinnamate | 3 |
| perfume | 0.3 |
| water qsp | 100 |

EXAMPLE 25

| ANTISEBORRHEIC CREAM | % by weight |
|---|---|
| polyethylene glycol stearate containing 20 moles of ethylene oxide | 3.85 |
| a mixture of mono- and di-stearate of non-autoemulsifiable glycerol | 1.20 |
| cetyl alcohol | 2.45 |
| liquid petrolatum | 5 |
| perhydrosqualene | 7 |
| isopropyl myristate | 1 |
| S—carboxymethyl cysteine | 2 |
| compound of the formula | |

-continued

| ANTISEBORRHEIC CREAM | % by weight |
|---|---|
| $$\begin{array}{c}\text{CH}_3\\|\\\text{R---N}^{\oplus}\text{---CH}_2\text{---CO---HN---(CH}_2)_2\text{---NH---CO---CH}_2\text{---N---R}\\|\\\text{CH}_3\end{array}\quad\begin{array}{c}\text{CH}_3\\|\\\\|\\\text{CH}_3\end{array}$$ | 0.1 |
| R is a tallow chain | |
| perfume | 0.3 |
| water qsp | 100 |

EXAMPLE 26

| ANTISEBORRHEIC CREAM | % by weight |
|---|---|
| polyethyleneglycol stearate containing 20 moles of ethylene oxide | 6.60 |
| mixture of mono- and di-stearate of non-autoemulsifiable glycerol | 0.70 |
| cetyl alcohol | 4.20 |
| liquid petrolatum | 7 |
| perhydrosqualene | 5 |
| isopropylmyristate | 3 |
| S—carboxymethyl cysteine | 1 |
| compound of the formula | 0.3 |
| $$\begin{array}{c}\text{CH}_3\\|\\\text{R---N}^{\oplus}\text{---CH}_2\text{---CO---HN---(CH}_2)_2\text{---NH---CO---CH}_2\text{---N---R}\\|\\\text{CH}_3\end{array}\quad\begin{array}{c}\text{CH}_3\\|\\\\|\\\text{CH}_3\end{array}$$ | 0.3 |
| R is a tallow chain | |
| perfume | 0.3 |
| water qsp | 100 |

One observes a softness to the touch after treatment with one of these compositions intended to be applied to the skin.

The various tradenames used in the preceding Examples are explained in greater detail below.

POLAWAX GP 200: oxyethyleneated stearyl alcohol sold by Croda.

ALFOL C16/C18 (50/50): cetyl/stearyl alcohol sold by Condea.

CELLOSIZE QP 4400 H: hydroxyethylcellulose having a viscosity of 4,400 cps at 25° C. in a 2% strength solution (measured using a Brookfield No. 4 module), sold by Union Carbide.

CROTEIN Q: quaternized protein hydrolysate derivative sold by Croda.

GAFQUAT 755: quaternary polyvinylpyrrolidone copolymer having a molecular weight of 1,000,000, marketed by GENERAL ANILINE.

MERQUAT: dimethyldialkyl chloride homopolymer sold by Merck.

SINNOWAX 40: cetyl/stearyl alcohol containing 20% of alcohol oxyethyleneated with 15 mols of ethylene oxide, marketed by Henkel.

UKANIL 25: linear fatty alcohol (C$_{13}$-C$_{15}$) oxyethyleneated with 2.8 mols of ethylene oxide, sold by PUK.

UKANIL 43: linear fatty alcohol (C$_{13}$-C$_{15}$) oxyethyleneated with 7 mols of ethylene oxide, sold by PUK.

SETACIN 103 SPEZIAL: sodium hemi-sulphosuccinate of polyoxyethyleneated lauryl alcohol, containing 40% of active ingredient, sold by Zschimmer and Schwarz.

METHOCEL F 4M: hydroxypropylmethylcellulose sold by Dow Chemical.

MIRANOL C 2M: cycloimidazoline derivative of coconut oil (38% active material) of the formula

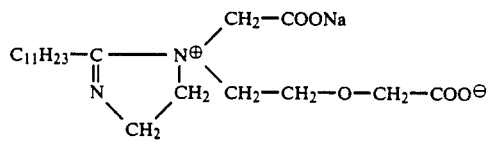

sold by Miranol

AMERCHOL L 101: Light mineral oil and a mixture of alcohol and sterols of lanoline sold by American Cholesterol Products Inc NATROSOL 250 HHR: hydroxy ethyl ether of cellulose sold by HERCULES

We claim:

1. A composition for the treatment of hair to improve the combing-out, the softness and the glossiness properties of hair, and of skin to impart softness to the touch properties thereto, said composition containing in a cosmetically acceptable medium at least one bis-(quaternary ammonium) derivative having two lipophilic chains and having the formula

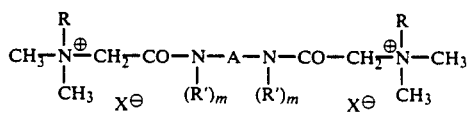

wherein

R represents a saturated or unsaturated, linear or branched aliphatic group having from 8 to 22 carbon atoms or a fatty chain derived from tallow, lanolin or copra, A represents —(CH$_2$)$_n$— wherein n represents an integer ranging from 1 to 18, in which case R' represents hydrogen and m=1, or A, together with the nitrogen atoms to which it is attached, represents a heterocyclic group, in which case m=0, and X$^-$ represent an anion derived from a mineral or organic acid, said bis-(quaternary ammonium) derivative being present in an amount of 0.01 to 10 percent by weight of said composition and an effective amount of a sun filter agent.

2. A composition for the treatment of hair to improve the combing-out, the softness and the glossiness properties of hair, and of skin to impart softness to the touch properties thereto, said composition containing in a cosmetically acceptable medium at least one bis-(quaternary ammonium) derivative having two lipophilic chains and having the formula

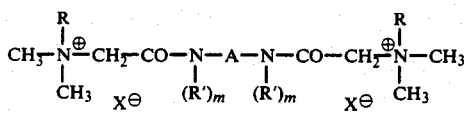

wherein

R represents a saturated or unsaturated, linear or branched aliphatic group having from 8 to 22 carbon atoms or a fatty chain derived from tallow, lanolin or copra, A represents —(CH$_2$)$_n$— wherein n represents an integer ranging from 1 to 18, in which case R' represents hydrogen and m=1, or A, together with the nitrogen atoms to which it is attached, represents a heterocyclic group, in which case m=0, and X$^-$ represents an anion derived from a mineral or organic acid, said bis-(quaternary ammonium) derivative being present in an amount of 0.01 to 10 percent by weight of said composition, and an effective amount of an oxidation hair dye.

3. A composition for the treatment of hair to improve the combing-out, the softness and the glossiness properties of hair, and of skin to impart softness to the touch properties thereto, said composition containing in a cosmetically acceptable medium at least one bis-(quaternary ammonium) derivative having two lipophilic chains and having the formula

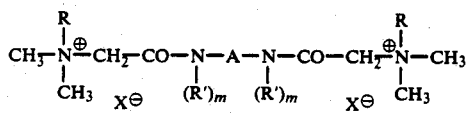

wherein

R represents a saturated or unsaturated, linear or branched aliphatic group having from 8 to 22 carbon atoms or a fatty chain derived from tallow, lanolin or copra, A represents —(CH$_2$)$_n$— wherein n represents an integer ranging from 1 to 18, in which case R' represents hydrogen and m=1, or A, together with the nitrogen atoms to which it is attached, represents a heterocyclic group, in which case m=0, and X$^-$ represents an anion derived from a mineral or organic acid, said bis-(quaternary ammonium) derivative being present in an amount of 0.01 to 10 percent by weight of said composition, and an effective amount of a reducing agent for opening the S—S bonds of the keratin of the hair.

4. The composition of claim 3 wherein said reducing agent is thioglycolic acid or thioglycerol.

5. A composition for the treatment of hair to improve the combing-out, the softness and the glossiness properties of hair, and of skin to impart softness to the touch properties thereto, said composition containing in a cosmetically acceptable medium at least one bis-(quaternary ammonium) derivative having two lipophilic chains and having the formula

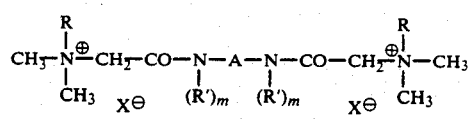

wherein

R represents a saturated or unsaturated, linear or branched aliphatic group from 8 to 22 carbon atoms or a fatty chain derived from tallow, lanolin or copra, A represents —(CH$_2$)$_n$— wherein n represents an integer ranging from 1 to 18, in which case R' represents hydrogen and m=1, or A, together with the nitrogen atoms to which it is attached, represents a heterocyclic group, in which case m=0, and X$^-$ represents an anion derived from a mineral or organic acid, said bis-(quaternary ammonium) derivative being present in an amount of 0.01 to 10 percent by weight of said composition, and an effective amount of an oxidizing agent.

6. The composition of claim 5 wherein the oxidizing agent is hydrogen peroxide.

7. A composition for the treatment of hair to improve the combing-out, the softness and the glossiness properties of hair, and of skin to impart softness to the touch properties thereto, said composition containing in a cosmetically acceptable medium at least one bis-(quaternary ammonium) derivative having two lipophilic chains and having the formula

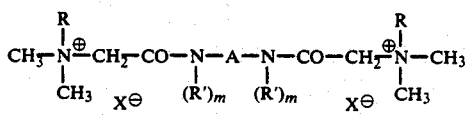

wherein

R represents a saturated or unsaturated, linear or branched aliphatic group having from 8 to 22 carbon atoms or a fatty chain derived from tallow, lanolin or copra, A represents —(CH$_2$)$_n$— wherein n represents an integer ranging from 1 to 18, in which case R' represents hydrogen and m=1, or A, together with the nitrogen atoms to which it is attached, represents a heterocyclic group, in which case m=0, and X⁻ represents an anion derived from a mineral or organic acid, said bis-(quaternary ammonium) derivative being present in an amount of 0.01 to 10 percent by weight of said composition, and an effective amount of a quaterized or non-quaternized protein hydrolysate.

8. A composition for the treatment of hair to improve the combing-out, the softness and the glossiness properties of hair, and of skin to impart softness to the touch properties thereto, said composition containing in a cosmetically acceptable medium at least one bis-(quaternary ammonium) derivative having two lipophilic chains and having the formula

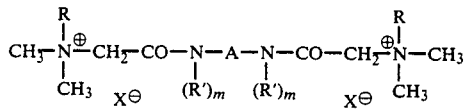

wherein

R represents a saturated or unsaturated, linear or branched aliphatic group having from 8 to 22 carbon atoms or a fatty chain derived from tallow, lanolin or copra, A represents —(CH$_2$)$_n$— wherein n represents an integer ranging from 1 to 18, in which case R' represents hydrogen and m=1, or A, together with the nitrogen atoms to which it is attached, represents a heterocyclic group, in which case m=0, and X⁻ represents an anion derived from a mineral or organic acid, said bis-(quaternary ammonium) derivative being present in an amount of 0.01 to 10 percent by weight of said composition, and an effective amount of an antiseborrhea agent.

9. The composition of claim 8 wherein said antiseborrhea agent is S-carboxymethyl cysteine.

10. A composition for the treatment of hair to improve the combing-out, the softness and the glossiness properties of hair, and of skin to impart softness to the touch properties thereto, said composition containing in a cosmetically acceptable medium at least one bis-(quaternary ammonium) derivative having two lipophilic chains and having the formula

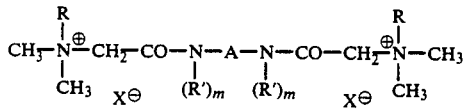

wherein

R represents a saturated or unsaturated, linear or branched aliphatic group having from 8 to 22 carbon atoms or a fatty chain derived from tallow, lanolin or copra, A represents —(CH$_2$)$_n$— wherein n represents an integer ranging from 1 to 18, in which case R' represents hydrogen and m=1, or A, together with the nitrogen atoms to which it is attached, represents a heterocyclic group, in which case m=0, and X⁻ represents an anion derived from a mineral or organic acid, said bis-(quaternary ammonium) derivative being present in an amount of 0.01 to 10 percent by weight of said composition, and an effective amount of a hair structuring agent.

11. The composition of claim 10 wherein the hair structuring agent is dimethylolethylene thiourea.

12. A composition for the treatment of hair to improve the combing-out, the softness and the glossiness properties of hair, and of skin to impart softness to the touch properties thereto, said composition containing in a cosmetically acceptable medium at least one bis-(quaternary ammonium) derivative having two lipophilic chains and having the formula

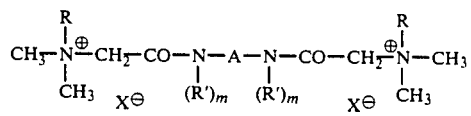

wherein

R represents alkyl or alkenyl containing 12–18 carbon atoms,

A represents —(CH$_2$)$_n$— wherein n represents an integer ranging from 1 to 18, in which case R' represents hydrogen and m=1, or A, together with the nitrogen atoms to which it is attached, represents a heterocyclic group, in which case m=0, and X⁻ represents an anion derived from a mineral or organic acid, said bis-(quaternary ammonium) derivative being present in an amount of 0.01 to 10 percent by weight of said composition.

13. A composition for the treatment of hair to improve the combing-out, the softness and the glossiness properties of hair, and of skin to impart softness to the touch properties thereto, said composition containing in a cosmetically acceptable medium at least one bis-(quaternary ammonium) derivative having two lipophilic chains and having the formula

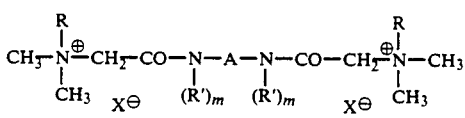

wherein

R represents a fatty chain derived from tallow,

A represents —(CH$_2$)$_n$— wherein n represents an integer ranging from 1 to 18, in which R' represents hydrogen and m=1, or A, together with the nitrogen atoms to which it is attached, represents a heterocyclic group, in which case m=0, and X⁻ represents an anion derived from a mineral or organic acid, said bis-(quaternary ammonium) derivative being present in an amount of 0.01 to 10 percent by weight of said composition.

14. A composition for the treatment of hair to improve the combing-out, the softness and the glossiness properties of hair, and of skin to impart softness to the touch properties thereto, said composition containing in a cosmetically acceptable medium at least one bis-(quaternary ammonium) derivative having two lipophilic chains and having the formula

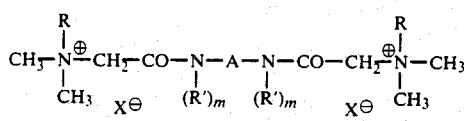

wherein
- R represents a saturated or unsaturated, linear or branched aliphatic group having from 8 to 22 carbon atoms or a fatty chain derived from tallow, lanolin or copra,
- A, together with the nitrogen atoms to which it is attached, represent piperazinyl, in which case m=0, and
- $X^-$ represents an anion derived from a mineral or organic acid,
- said bis-(quaternary ammonium) derivative being present in an amount of 0.01 to 10 percent by weight of said composition.

15. A composition for the treatment of hair to improve the combing-out, the softness and the glossiness properties of hair, and of skin to impart softness to the touch properties thereto, said composition containing in a cosmetically acceptable medium at least one bis-(quaternary ammonium) derivative having two lipophilic chains and having the formula

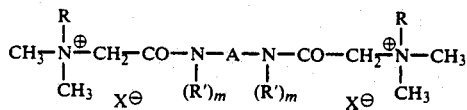

wherein
- R represents a saturated or unsaturated, linear or branched aliphatic group having from 8 to 22 carbon atoms or a fatty chain derived from tallow, lanolin or copra,
- A represents —$(CH_2)_n$— wherein n represents an integer ranging from 1 to 18, in which case R' represents hydrogen and m=1, or
- A, together with the nitrogen atoms to which it is attached represents a heterocyclic group, in which case m=0, and
- $X^-$ represents an anion derived from a mineral or organic acid,
- said bis-(quaternary ammonium) derivative being present in an amount of 0.01 to 10 percent by weight of said composition, said composition being in the form of a cream, a gel, an emulsion, a powder or an aerosol packaged in an aerosol container.

16. A shampoo composition which facilitates the combing-out of the hair when wet or dry and which imparts glossiness, softness, suppleness, manageability and antistatic properties to the hair when dry comprising in an aqueous medium at least one bis-(quaternary ammonium) derivative having two lipophilic chains and having the formula

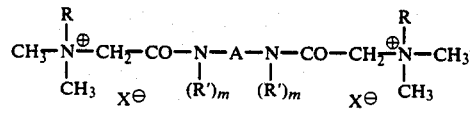

wherein
- R represent a saturated or unsaturated, linear or branched aliphatic group having from 8 to 22 carbon atoms or a fatty chain derived from tallow, lanolin or copra,
- A represents —$(CH_2)_n$—O wherein n represents an integer ranging from 1 to 18, in which case R' represents hydrogen and m=1, or
- A, together with the nitrogen atoms to which it is attached, represents a heterocyclic group, in which case m=0, and
- $X^-$ represents an anion derived from a mineral or organic acid,
- said bis-(quaternary ammonium) derivative being present in an amount of 0.01 to 10 percent by weight of said composition, and
- at least one anionic, non-ionic or amphoteric surface-active agent, or a mixture thereof, present in an amount ranging from 2 to 50 percent by weight of said shampoo composition.

17. The shampoo composition of claim 16 wherein
- R represents a mixture of $C_{12}$-$C_{14}$ alkyls or a fatty chain derived from tallow,
- A represents —$(CH_2)_n$— wherein n represents an integer ranging from 1 to 18, in which case R' represents hydrogen and m=1, or
- A, together with the nitrogen atoms to which it is attached, represents piperazinyl, in which case m=0.

18. The shampoo composition of claim 16 wherein said bis-(quaternary ammonium) derivative is selected from the group consisting of

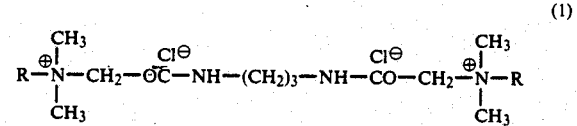

wherein R=a fatty chain derived from tallow,

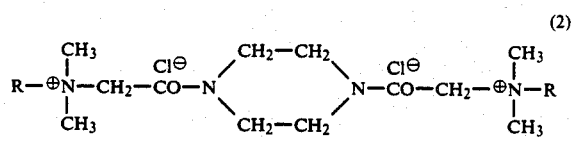

wherein R=a fatty chain derived from tallow,

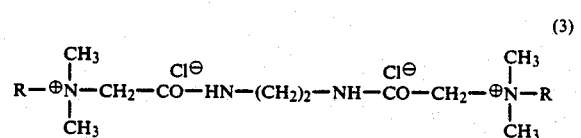

wherein R=a fatty chain derived from tallow,

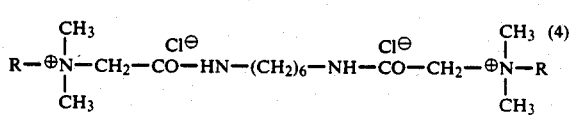

wherein R=a fatty chain derived from tallow, and $$\begin{array}{c} \text{CH}_3 \\ | \\ \text{R}-\overset{\oplus}{\text{N}}-\text{CH}_2-\text{CO}-\text{HN}-(\text{CH}_2)_6-\text{NH}-\text{CO}-\text{CH}_2-\overset{\oplus}{\text{N}}-\text{R} \\ | \\ \text{CH}_3 \qquad \text{Cl}^\ominus \qquad \text{Cl}^\ominus \qquad | \\ \text{CH}_3 \end{array} \quad (5)$$

wherein R = a mixture of alkyl chains having 12–14 carbon atoms.

19. A hair dye composition comprising in an aqueous medium having a pH ranging from 8 to 11, at least one bis-(quaternary ammonium) derivative having two lipophilic chains and having the formula $$\begin{array}{c} \text{R} \qquad\qquad\qquad\qquad\qquad\qquad\qquad\qquad \text{R} \\ \overset{\oplus}{|} \qquad\qquad\qquad\qquad\qquad\qquad\qquad\qquad \overset{\oplus}{|} \\ \text{CH}_3-\text{N}-\text{CH}_2-\text{CO}-\text{N}-\text{A}-\text{N}-\text{CO}-\text{CH}_2-\text{N}-\text{CH}_3 \\ | \qquad\qquad\qquad | \qquad\qquad | \qquad\qquad | \\ \text{CH}_3 \; \text{X}^\ominus \quad (\text{R}')_m \quad (\text{R}')_m \quad \text{X}^\ominus \; \text{CH}_3 \end{array}$$

wherein
R represents a saturated or unsaturated, linear or branched aliphatic group having from 8 to 22 carbon atoms or a fatty chain derived from tallow, lanolin or copra,
A represents —(CH$_2$)$_n$— wherein n represents an integer ranging from 1 to 18, in which case R' represents hydrogen and m=1, or
A, together with the nitrogen atoms to which it is attached, represents a heterocyclic group, in which case m=0, and
X$^-$ represents an anion derived from a mineral or organic acid,
said bis-(quaternary ammonium) derivative being present in an amount of 0.01 to 10 percent by weight of said composition, and
an effective amount of a hair dye to dye said hair.

20. The hair dye composition of claim 19 wherein
R represents a mixture of C$_{12}$–C$_{14}$ alkyls or a fatty chain derived from tallow,
A represents —(CH$_2$)$_n$— wherein n represents an integer ranging from 1 to 18, in which case R' represents hydrogen and m=1, or
A, together with the nitrogen atoms to which it is attached, represents piperazinyl, in which case m=0.

21. The hair dye composition of claim 19 wherein said bis-(quaternary ammonium) derivative is selected from the group consisting of $$\begin{array}{c} \text{CH}_3 \\ \overset{\oplus}{|} \\ \text{R}-\text{N}-\text{CH}_2-\text{OC}-\text{NH}-(\text{CH}_2)_3-\text{NH}-\text{CO}-\text{CH}_2-\overset{\oplus}{\text{N}}-\text{R} \\ | \qquad \text{Cl}^\ominus \qquad\qquad\qquad \text{Cl}^\ominus \qquad | \\ \text{CH}_3 \qquad\qquad\qquad\qquad\qquad\qquad\qquad \text{CH}_3 \end{array} \quad (1)$$

wherein R = a fatty chain derived from tallow, $$\begin{array}{c} \text{CH}_3 \qquad\qquad \text{CH}_2-\text{CH}_2 \qquad\qquad \text{CH}_3 \\ | \qquad\qquad / \qquad\qquad \backslash \qquad\qquad | \\ \text{R}-\overset{\oplus}{\text{N}}-\text{CH}_2-\text{CO}-\text{N} \qquad\qquad \text{N}-\text{CO}-\text{CH}_2-\overset{\oplus}{\text{N}}-\text{R} \\ | \qquad \text{Cl}^\ominus \; \backslash \qquad\qquad / \; \text{Cl}^\ominus \; | \\ \text{CH}_3 \qquad\qquad \text{CH}_2-\text{CH}_2 \qquad\qquad \text{CH}_3 \end{array} \quad (2)$$

wherein R = a fatty chain derived from tallow, $$\begin{array}{c} \text{CH}_3 \qquad\qquad\qquad\qquad\qquad\qquad\qquad \text{CH}_3 \\ | \qquad\qquad\qquad\qquad\qquad\qquad\qquad\qquad | \\ \text{R}-\overset{\oplus}{\text{N}}-\text{CH}_2-\text{CO}-\text{HN}-(\text{CH}_2)_2-\text{NH}-\text{CO}-\text{CH}_2-\overset{\oplus}{\text{N}}-\text{R} \\ | \qquad \text{Cl}^\ominus \qquad\qquad\qquad \text{Cl}^\ominus \qquad | \\ \text{CH}_3 \qquad\qquad\qquad\qquad\qquad\qquad\qquad \text{CH}_3 \end{array} \quad (3)$$

wherein R = a fatty chain derived from tallow, $$\begin{array}{c} \text{CH}_3 \qquad\qquad\qquad\qquad\qquad\qquad\qquad \text{CH}_3 \\ | \qquad\qquad\qquad\qquad\qquad\qquad\qquad\qquad | \\ \text{R}-\overset{\oplus}{\text{N}}-\text{CH}_2-\text{CO}-\text{HN}-(\text{CH}_2)_6-\text{NH}-\text{CO}-\text{CH}_2-\overset{\oplus}{\text{N}}-\text{R} \\ | \qquad \text{Cl}^\ominus \qquad\qquad\qquad \text{Cl}^\ominus \qquad | \\ \text{CH}_3 \qquad\qquad\qquad\qquad\qquad\qquad\qquad \text{CH}_3 \end{array} \quad (4)$$

wherein R = a fatty chain derived from tallow, and $$\begin{array}{c} \text{CH}_3 \qquad\qquad\qquad\qquad\qquad\qquad\qquad \text{CH}_3 \\ | \qquad\qquad\qquad\qquad\qquad\qquad\qquad\qquad | \\ \text{R}-\overset{\oplus}{\text{N}}-\text{CH}_2-\text{CO}-\text{HN}-(\text{CH}_2)_6-\text{NH}-\text{CO}-\text{CH}_2-\overset{\oplus}{\text{N}}-\text{R} \\ | \qquad \text{Cl}^\ominus \qquad\qquad\qquad \text{Cl}^\ominus \qquad | \\ \text{CH}_3 \qquad\qquad\qquad\qquad\qquad\qquad\qquad \text{CH}_3 \end{array} \quad (5)$$

wherein R = a mixture of alkyl chains having 12–14 carbon atoms.

22. A reducing composition for the first stage of a permanent wave operation wherein the S—S bonds in the keratin of the hair are opened comprising in an aqueous medium at least one bis-(quaternary ammonium) derivative having two lipophilic chains and having the formula $$\begin{array}{c} \text{R} \qquad\qquad\qquad\qquad\qquad\qquad\qquad\qquad \text{R} \\ \overset{\oplus}{|} \qquad\qquad\qquad\qquad\qquad\qquad\qquad\qquad \overset{\oplus}{|} \\ \text{CH}_3-\text{N}-\text{CH}_2-\text{CO}-\text{N}-\text{A}-\text{N}-\text{CO}-\text{CH}_2-\text{N}-\text{CH}_3 \\ | \qquad\qquad\qquad | \qquad\qquad | \qquad\qquad | \\ \text{CH}_3 \; \text{X}^\ominus \quad (\text{R}')_m \quad (\text{R}')_m \quad \text{X}^\ominus \; \text{CH}_3 \end{array}$$

wherein
R represents a saturated or unsaturated, linear or branched aliphatic group having from 8 to 22 carbon atoms or a fatty chain derived from tallow, lanolin or copra,
A represents —(CH$_2$)$_n$— wherein n represents an integer ranging from 1 to 18, in which case R' represents hydrogen and m=1, or
A, together with the nitrogen atoms to which it is attached, represents a heterocyclic group, in which case m=0, and
X$^-$ represents an anion derived from a mineral or organic acid,
said bis-(quaternary ammonium) derivative being present in an amount of 0.1 to 10 percent by weight of said composition, and
a reducing agent for opening the S—S bonds of the keratin of the hair present in an amount ranging from 1 to 11 percent by weight of said reducing composition, said composition having a pH ranging from 7 to 10.

23. The reducing composition of claim 22 wherein
R represents a mixture of C$_{12}$–C$_{14}$ alkyls or a fatty chain derived from tallow,
A represents —(CH$_2$)$_n$— wherein n represents an integer ranging from 1 to 18, in which case R' represents hydrogen and m=1, or
A, together with the nitrogen atoms to which it is attached, represents piperazinyl, in which case m=0.

24. The reducing composition of claim 22 wherein said bis-(quaternary ammonium) derivative is selected from the group consisting of

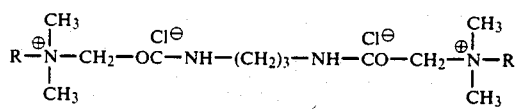

wherein R = a fatty chain derived from tallow,

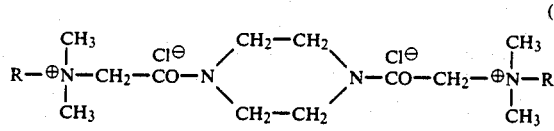

wherein R = a fatty chain derived from tallow,

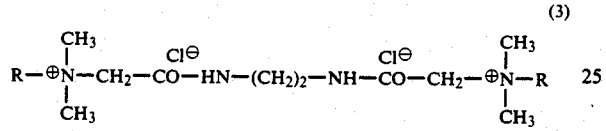

wherein R = a fatty chain derived from tallow,

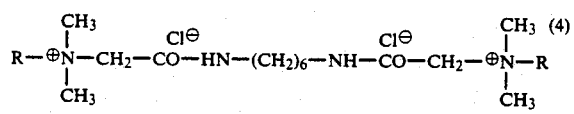

wherein R = a fatty chain derived from tallow, and

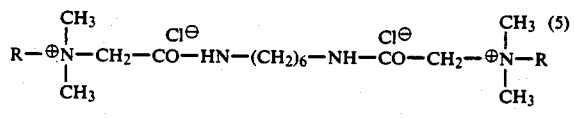

wherein R = a mixture of alkyl chains having 12–14 carbon atoms.

25. A process for treating the hair to improve the combing-out, the softness and the glossiness properties of the hair, and for treating the skin to impart softness to the touch properties thereto comprising applying to the hair or skin a composition containing in a cosmetically acceptable medium at least one bis-(quaternary ammonium) derivative having two lipophilic chains and having the formula

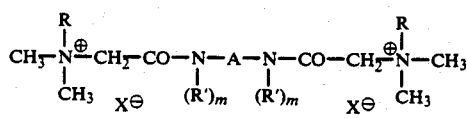

wherein
R represents a saturated or unsaturated, linear or branched aliphatic group having from 8 to 22 carbon atoms or a fatty chain derived from tallow, lanolin or copra, A represents —$(CH_2)_n$— wherein n represents an integer ranging from 1 to 18, in which case R' represents hydrogen and m=1, or A, together with the nitrogen atoms to which it is attached, represents a heterocyclic group, in which case m=0, and $X^-$ represents an anion derived from a mineral or organic acid, said bis-(quaternary ammonium) derivative being present in an amount of 0.01 to 10 percent by weight of said composition.

26. The process of claim 25 wherein

R represents a mixture of $C_{12}$–$C_{14}$ alkyls or a fatty chain derived from tallow, A represents —$(CH_2)_n$— wherein n represents an integer ranging from 1 to 18, in which case R' represents hydrogen and m=1, or A, together with the nitrogen atoms to which it is attached, represents piperazinyl, in which case m=0.

27. The process of claim 25 wherein said bis-(quaternary ammonium) derivative is selected from the group consisting of

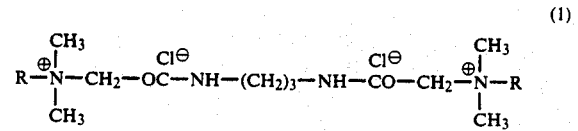

wherein R = a fatty chain derived from tallow,

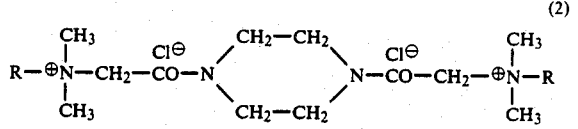

wherein R = a fatty chain derived from tallow,

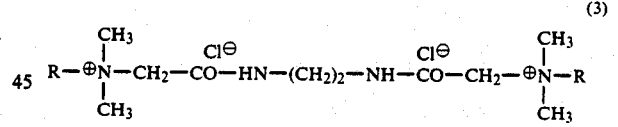

wherein R = a fatty chain derived from tallow,

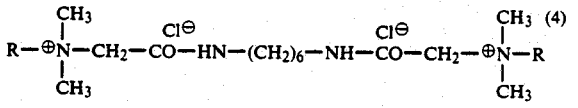

wherein R = a fatty chain drived from tallow, and

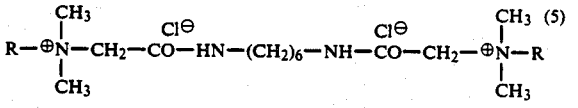

wherein R = a mixture of alkyl chains having 12–14 carbon atoms.

* * * * *